(12) United States Patent
Boularot et al.

(10) Patent No.: US 9,730,586 B2
(45) Date of Patent: Aug. 15, 2017

(54) APPARATUS AND METHOD FOR BRAIN FIBER BUNDLE MICROSCOPY

(71) Applicant: Mauna Kea Technologies, Paris (FR)

(72) Inventors: Nicolas Boularot, Champigny-sur-Marne (FR); Arnaud Cressant, Paris (FR)

(73) Assignee: Mauna Kea Technologies, Paris (FR)

( * ) Notice: Subject to any disclaimer, the term of this patent is extended or adjusted under 35 U.S.C. 154(b) by 0 days.

(21) Appl. No.: 14/731,949

(22) Filed: Jun. 5, 2015

(65) Prior Publication Data

US 2015/0265153 A1   Sep. 24, 2015

Related U.S. Application Data

(62) Division of application No. 13/386,468, filed as application No. PCT/IB2010/002310 on Jul. 19, 2009, now Pat. No. 9,107,575.

(60) Provisional application No. 61/229,677, filed on Jul. 29, 2009.

(51) Int. Cl.
*A61B 5/00* (2006.01)
*A61B 1/00* (2006.01)
*G02B 23/26* (2006.01)
*A61B 90/11* (2016.01)
*A61B 1/313* (2006.01)

(52) U.S. Cl.
CPC ........ *A61B 5/0084* (2013.01); *A61B 1/00154* (2013.01); *A61B 5/6814* (2013.01); *A61B 5/6864* (2013.01); *A61B 5/6868* (2013.01); *A61B 5/6882* (2013.01); *A61B 90/11* (2016.02); *G02B 23/26* (2013.01); *A61B 1/313* (2013.01); *A61B 5/0068* (2013.01); *A61B 5/0071* (2013.01); *A61B 2503/40* (2013.01); *A61B 2560/063* (2013.01); *A61B 2562/0238* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,465,803 A | * | 9/1969 | Swanstrom | F16B 5/0208 411/349 |
| 5,338,139 A | * | 8/1994 | Swanstrom | F16B 5/0208 411/107 |
| 6,572,624 B2 | * | 6/2003 | U | A61B 19/201 606/130 |
| 8,788,021 B1 | * | 7/2014 | Flusberg | A61B 5/0059 356/318 |

* cited by examiner

*Primary Examiner* — Jennifer Dieterle
*Assistant Examiner* — Farshad Negarestan
(74) *Attorney, Agent, or Firm* — Osha Liang LLP

(57) ABSTRACT

An intracranial implant to position a fiber bundle to a specified region of a brain of an animal. The implant may include a base support to be fixed to a skull of the animal over an orifice drilled in the skull, a hollow conduit arranged through the base support to guide the fiber bundle to the brain of the animal through the drilled orifice and a first locking member arranged on the base support, to cooperate with a ferrule of the fiber bundle, the first locking member configured to lock the fiber bundle to the specified region of the brain of the animal.

4 Claims, 16 Drawing Sheets

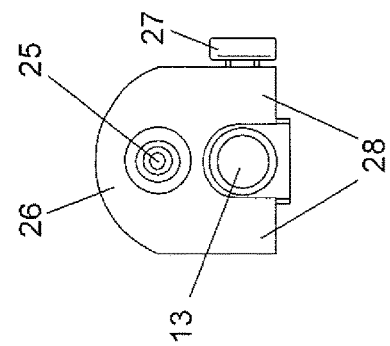
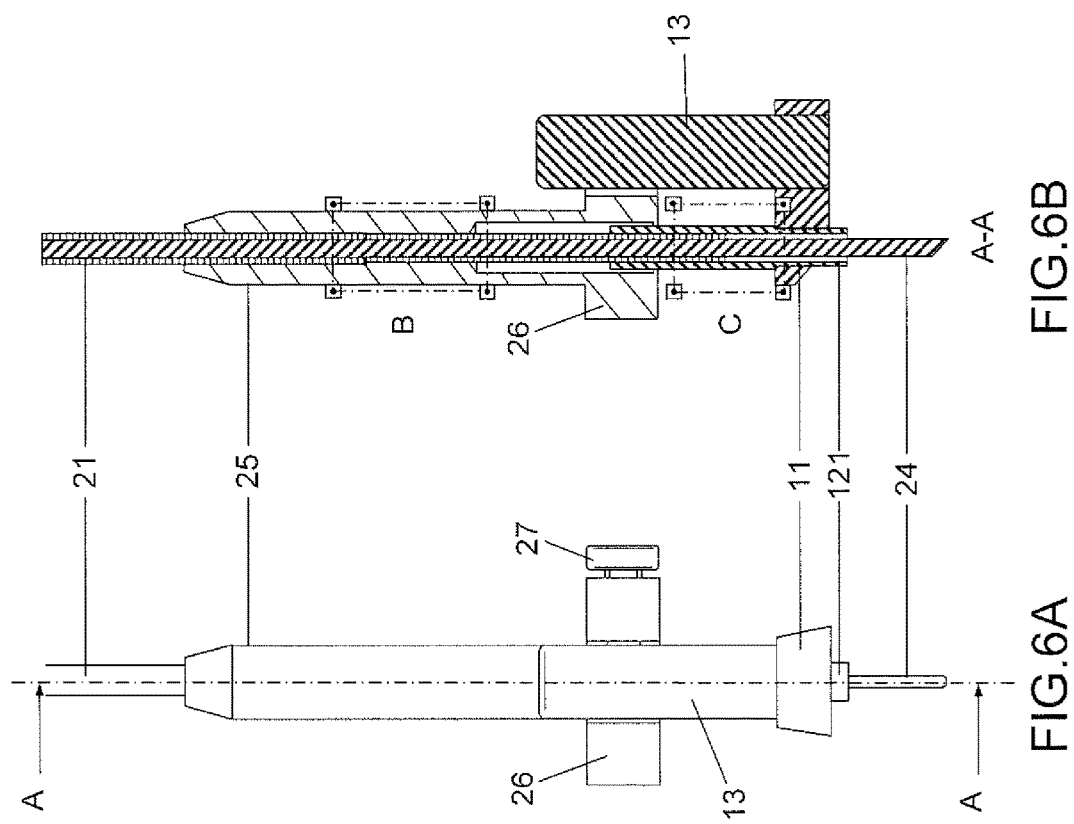

APPARATUS AND METHOD FOR BRAIN FIBER BUNDLE MICROSCOPY

CROSS-REFERENCE TO RELATED APPLICATIONS

This application is a divisional application and claims the benefit under 35 U.S.C. §120 of U.S. patent application Ser. No. 13/386,468, filed on Jan. 23, 2012, entitled "Apparatus and Method for Brain Fiber Bundle Microscopy," which is a national stage application of PCT/IB2010/002310, filed on Jul. 19, 2010, which claims priority to U.S. Provisional Application No. 61/229,677, filed on Jul. 29, 2009.

BACKGROUND

Field of the Present Disclosure

The disclosure relates to animal brain imaging. Particularly, the disclosure relates to brain imaging on wake behaving animals.

Background Art

Brain imaging on small animals may be implemented through different methods but only a few of them enable researchers to study selected regions of the central nervous systems with a spatial and time resolution sufficient to image the function of neural structures.

Indeed, magnetic resonance imaging and scanner imaging methods generally result in low resolution images only enabling to access functional information relating to activated brain regions. Methods using electrodes directly inserted into the brain for analyzing brain electrical sensitivity are as far hindered by a severe precision requirement in positioning the electrodes and by a complex interpretation of the resulting electric signals.

Microscopy methods have proven useful in brain imaging. Brain slices microscopy on deceased animals is well known but in vivo microscopy on a living animal is a recent subject. Historically, in vivo microscopy could not analyze deep-brain regions as the technique lacks satisfactory resolution or because it requires over-invasive surgery. The Applicant has described an approach for functional fiber-optic imaging of the intact mouse brain (Vincent et al., Live imaging of neural structure and function by fibred fluorescence microscopy. EMBO reports September 2006). The Applicant showed that fibered fluorescence microscopy which uses a small-diameter fiber-optic probe to provide real-time images has a spatial resolution enabling to image various neural structures in the living animal. This method has been useful in many physiological studies requiring the in situ functional imaging of tissues in a living anaesthetized animal.

Recently, a growing need to obtain images on freely moving animals and to make available chronic studies has emerged. Freely moving animal imaging requires high stability for images acquisition. Stanford University researchers have developed a bundle microscopy technology mounted on a mouse skull using an adapted helmet that enables freely moving studies (High speed, miniaturized fluorescence microscopy in freely moving mice. Benjamin Flusberg et al. Nature Methods, October 2008). However, this technology requires large coring in the mouse's brain and thereby prohibits deep-brain insertion. Additionally, the considerable helmet weight bans a truly free movement and the images resolution level limits the precision of the technology. Recently, the Applicant disclosed (Maskos et al., Functional fibered fluorescence imaging in freely moving mouse, poster No. 598.8 disclosed during the 38$^{th}$ annual meeting of the Society for Neurosciences 2008) the use of a minimally invasive probe securely fixed to the head with dental cement for fiber-optic microscopy imaging of neuronal networks in behaving animals. However, in order to acquire images on an extended period for chronic studies, there is a need to recalibrate the imaging system, therefore requiring to extract the probe out of the brain of the animal and to place it back. According to the current method, extracting the probe presents risk of breaking the tip of the bundle, thereby excluding reusing the same animal to carry out the study and involving incompatible maintenance costs to polish the broken probe.

The Applicant proposes hereinunder an intracranial implant for positioning a fiber bundle probe in the brain of an animal. The Applicant also proposes a fiber bundle probe adapted to said implant, a stereotactic device to manipulate said implant and probe, and a method for brain fiber bundle microscopy.

SUMMARY OF THE CLAIMED SUBJECT MATTER

In at least one aspect embodiments disclosed herein relate to an intracranial implant to position a fiber bundle to a specified region of a brain of an animal. The implant may include a base support to be fixed to a skull of the animal over an orifice drilled in the skull and a hollow conduit arranged through the base support to guide the fiber bundle to the brain of the animal through the drilled orifice. The implant may include a first locking member arranged on the base support, to cooperate with a ferrule of the fiber bundle, the first locking member configured to lock the fiber bundle to the specified region of the brain of the animal.

Other aspects and advantages of the disclosure will be apparent from the following description and the appended claims.

BRIEF DESCRIPTION OF DRAWINGS

FIGS. 6A, 6B and 6C illustrate respectively a lateral view, a transverse section and a top view of a fiber bundle probe according to an embodiment of the present disclosure cooperating with an implant according to an embodiment of the present disclosure.

DETAILED DESCRIPTION

Specific embodiments of the present disclosure will now be described in detail with reference to the accompanying Figures. Like elements in the various Figures may be denoted by like numerals.

Embodiments of the present disclosure relate to an intracranial implant to position a fiber bundle in a determined region of the brain of an animal, to a fiber bundle probe for brain fiber bundle microscopy, to a stereotactic device to manipulate an implant and a fiber bundle probe within a stereotactic frame and to a method for brain fiber bundle microscopy.

For example, the animal may be a transgenic mouse engineered to express specifically Green Fluorescent Proteins in several brain areas. A proximal tip of the fiber bundle may be connected to a system for confocal fluorescence microscopy imaging and a distal tip of the fiber bundle may be inserted in the brain of the animal.

In a method according to the present disclosure, the mouse may be anaesthetized and its head may be held in a stereotactic frame in order to drill an orifice in the skull of the animal and to precisely install an implant on the skull of the animal over said orifice.

Figure 1B:
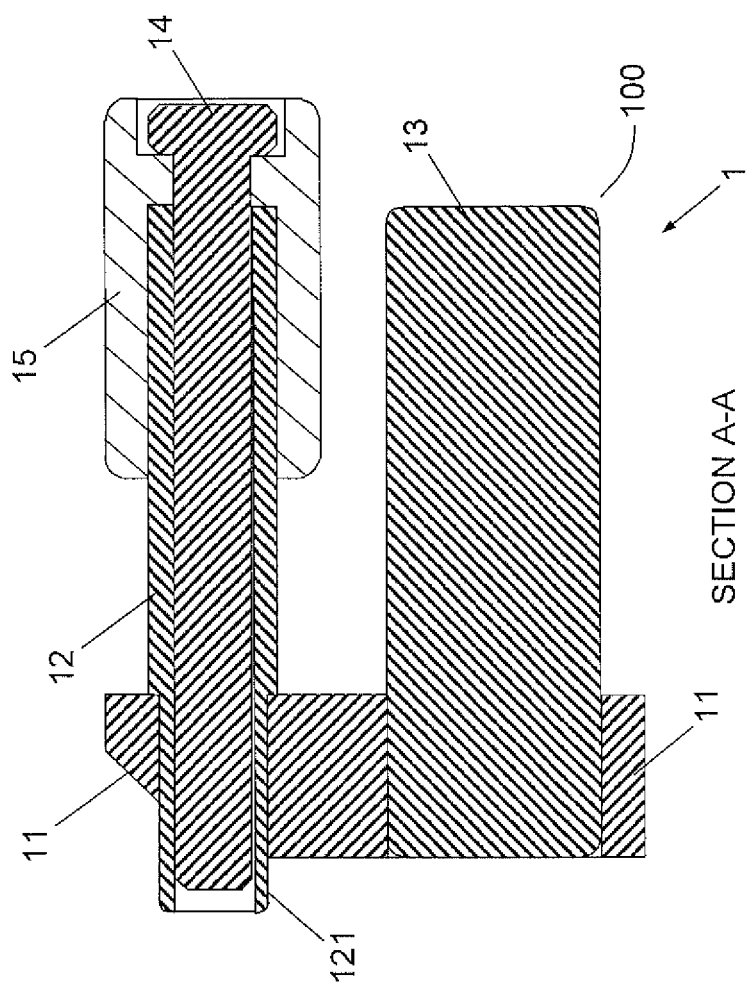
FIG. 1A and FIG. 1B illustrate respectively a top view and a longitudinal section of an implant with a cap according to an embodiment of the present disclosure.
Figure 1A:
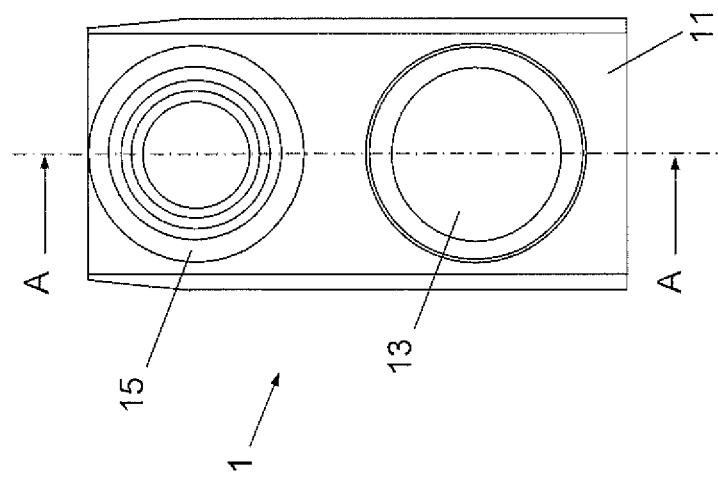

FIGS. 1A and 1B illustrate views of the implant according to an embodiment of the present disclosure. The implant 1 comprises a base support 11 to be fixed to the skull of the animal, an hollow conduit 12 arranged through the base support 11 and a first locking member 100 arranged on the base support 11 remote from the hollow conduit 12. FIG. 1 further shows a cap comprising an axis plug 14 having a body, that may be inserted in the hollow conduit 12, and a head surrounded by a helmet 15 for maintaining the axis plug 14 in the hollow conduit 12. The cap may be adapted to the implant 1 to avoid dirt to enter the hollow conduit 12, for example when the implant 1 is not used.

Figure 9:
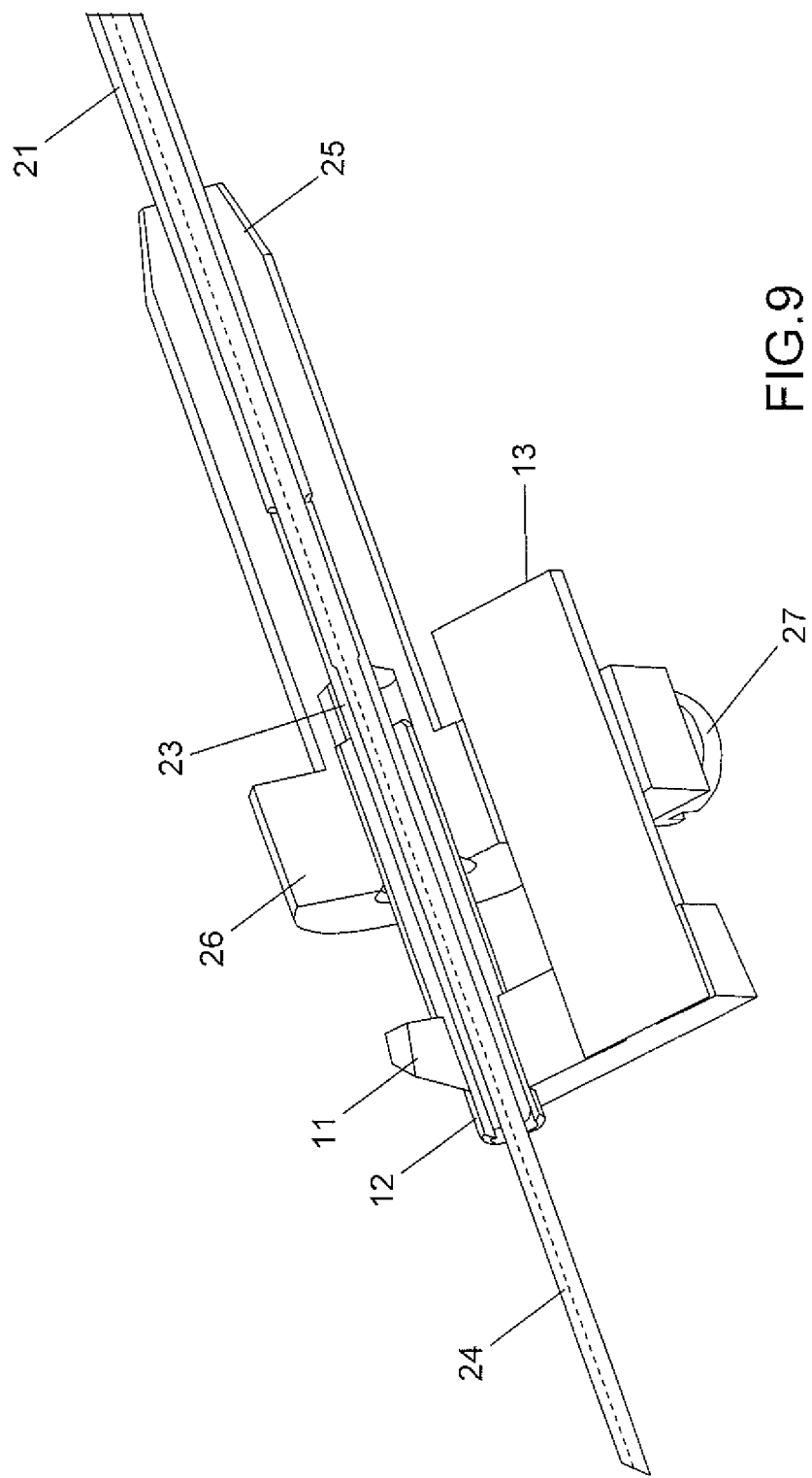
FIG. 9 is a perspective view of a transverse section of a Fiber bundle probe according to an embodiment of the present disclosure cooperating with an implant according to an embodiment of the present disclosure.

In the embodiment described on FIGS. 1A and 1B, the first locking member 100 may include a cylindrical pin 13, generally perpendicular to the base support 11, comprising a portion integral to said base support 11. As shown on FIG. 9, the pin 13 may be locked into a second locking member 26 arranged on a ferrule mounted on the fiber bundle 24 when the fiber bundle 24 is inserted in the hollow conduit 12 of the implant 1.

Figure 2:
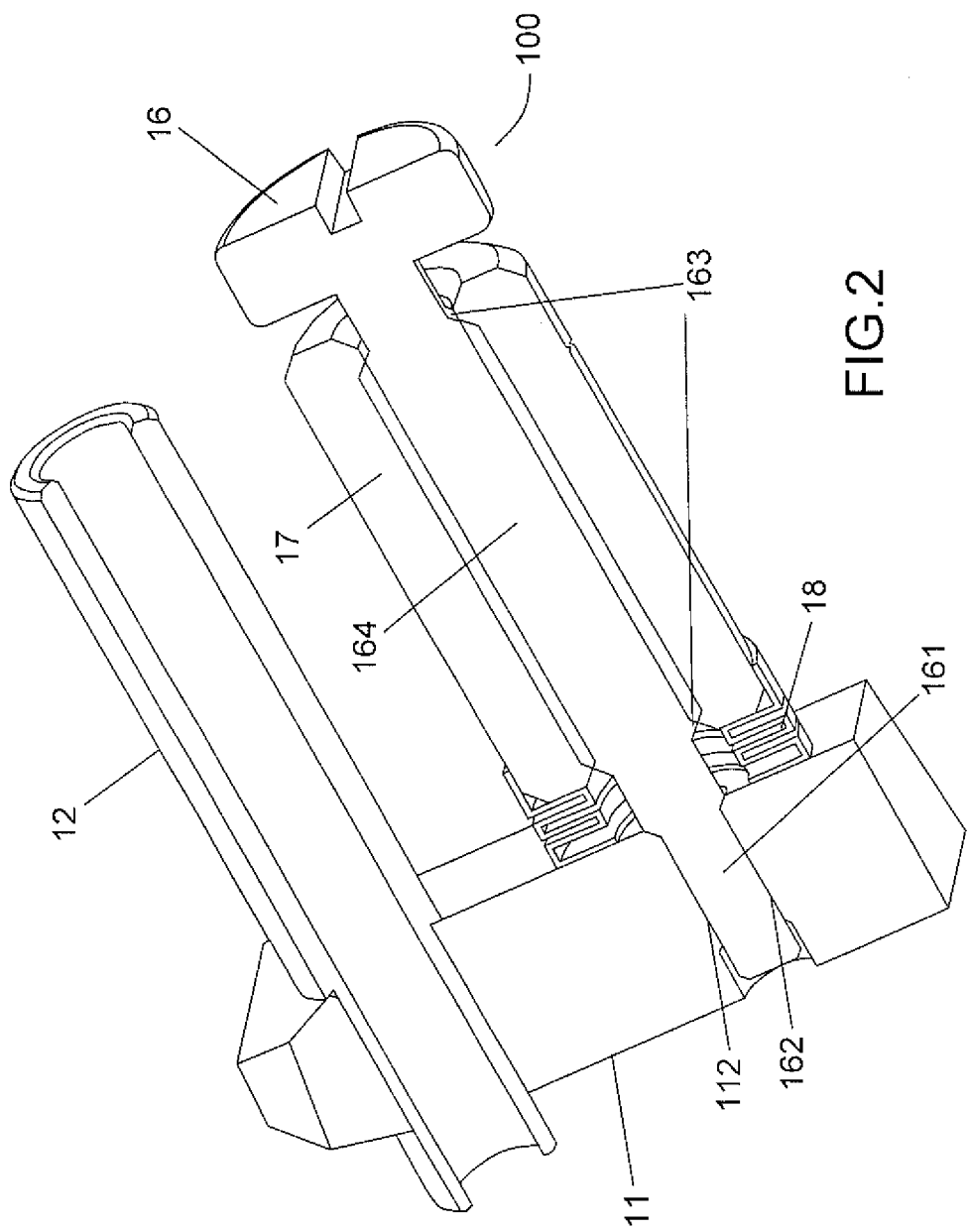
FIG. 2 illustrates a perspective view of a transverse section of an implant according to an embodiment of the present disclosure.
Figure 8:
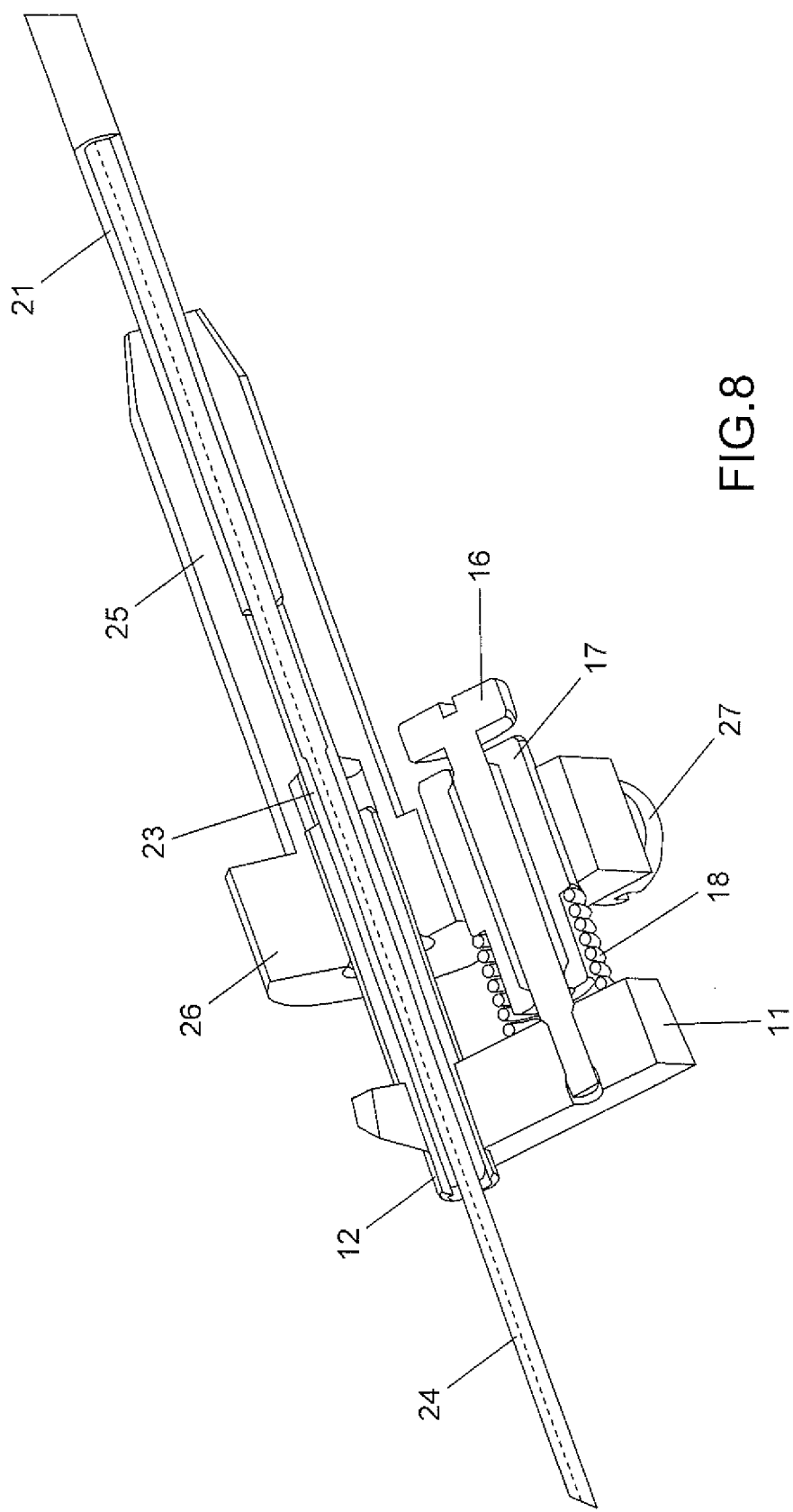
FIG. 8 is a perspective view of a transverse section of a fiber bundle probe according to an embodiment of the present disclosure cooperating with an implant according to an embodiment of the present disclosure.

In another embodiment described on FIG. 2, the first locking member 100 may comprise a screw 16 perpendicular to the base support 11 having a first portion 161 arranged in the base support and a second portion 164 around which a locking cylinder 17 is concentrically arranged. The locking cylinder 17 may be fixed in translation with regard to a longitudinal axis of the screw and free to rotate around said axis. The first portion 161 may comprise a first threading 162 cooperating with a second threading 112 of the base support 11 to adjust the position of the screw in a direction perpendicular to the base support 11. When the screw is threaded, the locking cylinder 17 may translate with regard to the longitudinal axis of the screw 16. As shown on FIG. 8, the first locking member comprising the screw 16 and the cylinder 17 is to be locked on the second locking member 26 of the ferrule arranged on the fiber bundle 24 using a locking screw 27 mounted on the second locking member 26, when the fiber bundle 24 is inserted in the hollow conduit 12 of the implant 1.

According to this embodiment, when the fiber bundle is inserted in the hollow conduit 12 of the implant and the second locking member of the ferrule arranged on the fiber bundle is fastened to the locking cylinder 17 of the first locking member to block the bundle on a determined position, it may be possible to adjust the position of the fiber bundle by adjusting the position of the locking cylinder 17. The first locking member may further comprise a toroid spring 18 concentrically arranged around the screw 16 at one end of the locking cylinder 17. The spring 18 enables compensation for play by pushing the screw 16 in the thread 112 and the locking cylinder 17 on the collar 163.

In another embodiment (not shown on FIG. 2), the first locking member may comprise a pin having a first portion arranged in the base support, said first portion being fixed in translation with regard to a longitudinal axis of the pin and free to rotate around said axis, and a second portion comprising a first threading cooperating with a second threading or a locking cylinder concentrically arranged around said second portion. A toroid spring may also be added for compensation of play as previously. This embodiment may also enable the adjustment of the position of the locking cylinder with regard to the base support.

Adjusting the position of the fiber bundle probe by screwing the screw 16 may be done without requiring to hold the head of the mouse in a stereotactic frame. Thereby, it may easily be done after the fiber bundle has been locked. When the fiber bundle is inserted in the brain of the animal, the brain tends to contract and it may occur that, in order to stay on a determined region of the brain to image, the fiber bundle positioning may be adjusted because of brain re-inflating.

One advantage of a locking mechanism comprising the first and second locking members is that it may block the fiber bundle on a determined region of the brain to image, preventing the fiber bundle to rotate around its longitudinal axis and to move in the hollow conduit where the fiber bundle is to be inserted. It may lead to increase stability for image acquisition, enabling the acquisition of images from a freely moving animal. Arranging the first locking member remote from the hollow conduit 12 where the fiber bundle is to be inserted may ease the fastening of the fiber bundle by reducing the required fastening torque. It may enable to avoid excessive constraint on the fiber bundle which may lead to equipment damages.

When the orifice has been drilled in the skull of the animal, the base support 11 of the implant may be fixed to the skull of the animal for the hollow conduit 12 to emerge onto the drilled orifice. Fixing the base support may be performed using for example micro-screws and dental cement.

Figure 10:
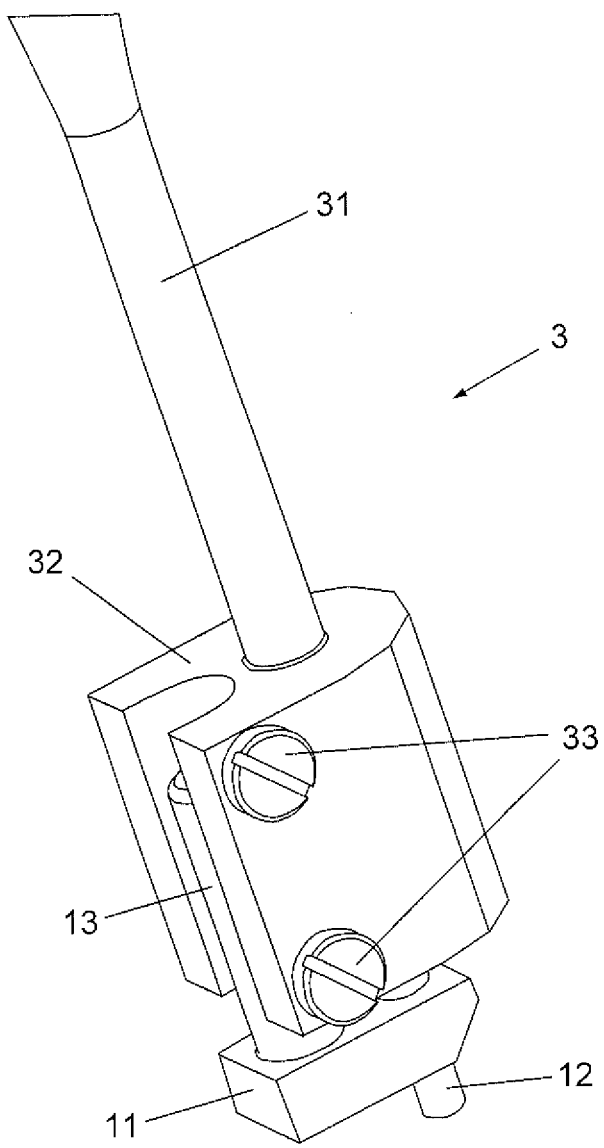
FIG. 10 is a perspective view of a stereotactic device according to an embodiment of the present disclosure manipulating an implant according to an embodiment of the present disclosure.

As shown on FIG. 10, the implant 1 may be manipulated with a stereotactic device 3 comprising a rod 31 connected to the stereotactic frame, and a groove 32 comprising screws 33 to fasten an object placed in the groove 32. The stereotactic device 3 is an interface that enables to manipulate the implant within the stereotactic frame. The implant 1 may placed on the skull of the animal horizontally with regard to an horizontal axis defined by the head of the animal in the stereotactic frame. As the skull of a mouse is curved, an amount of glue may be applied on the surface of the base support 11 in contact with the skull to compensate for slope.

Referring again to FIG. 1, the hollow conduit 12 may comprise a tube perpendicular to the base support 11 and may comprise an under part 121 extending beneath the base support 11. The under part 121 may enter the orifice drilled in the skull of the animal. In an embodiment, the under part 121 has a length adapted to penetrate in the brain of the animal. As the skull of a mouse is curved and the base support is installed horizontally, the length necessary to penetrate the brain may not be the same when the base support 11 is placed on different parts of the mouse's skull. In an embodiment, the length of the under part 121 is adapted for penetrating the brain when the base support 11 is fixed horizontally in any position of the mouse's skull. In another embodiment, the length or the under part 121 is adapted for penetrating the brain when the base support is fixed horizontally in at least one position on the skull of the mouse. In another embodiment, the length of the under part 121 is adapted for not entering the brain of the animal when the base support is fixed horizontally in any position of the mouse's skull.

The base support 11 may have a parallepipedic shape. Advantageously, the base support 11 may have a trapezoid based right prism shape, as shown on FIG. 6A. In this embodiment, the face or greater surface of said trapezoid based right prism is laid on the skull of the animal. As glue may be spread below said face and on the bevelled edges of the trapezoid prism, the base support 11 is accurately fixed on the mouse's skull. As shown on FIG. 1B, a base 111 of the trapezoid prism of the base support 11 close to the hollow conduit may advantageously be truncated for enabling an operator manipulating the base support 11 from aside to easily see the under part 121 of the hollow conduit 12. Thereby, the operator may accurately calibrate the stereotactic frame by easily targeting the bones of the skull of the mouse with the under part 121 of the implant mounted on the stereotactic device 3.

Figure 12:
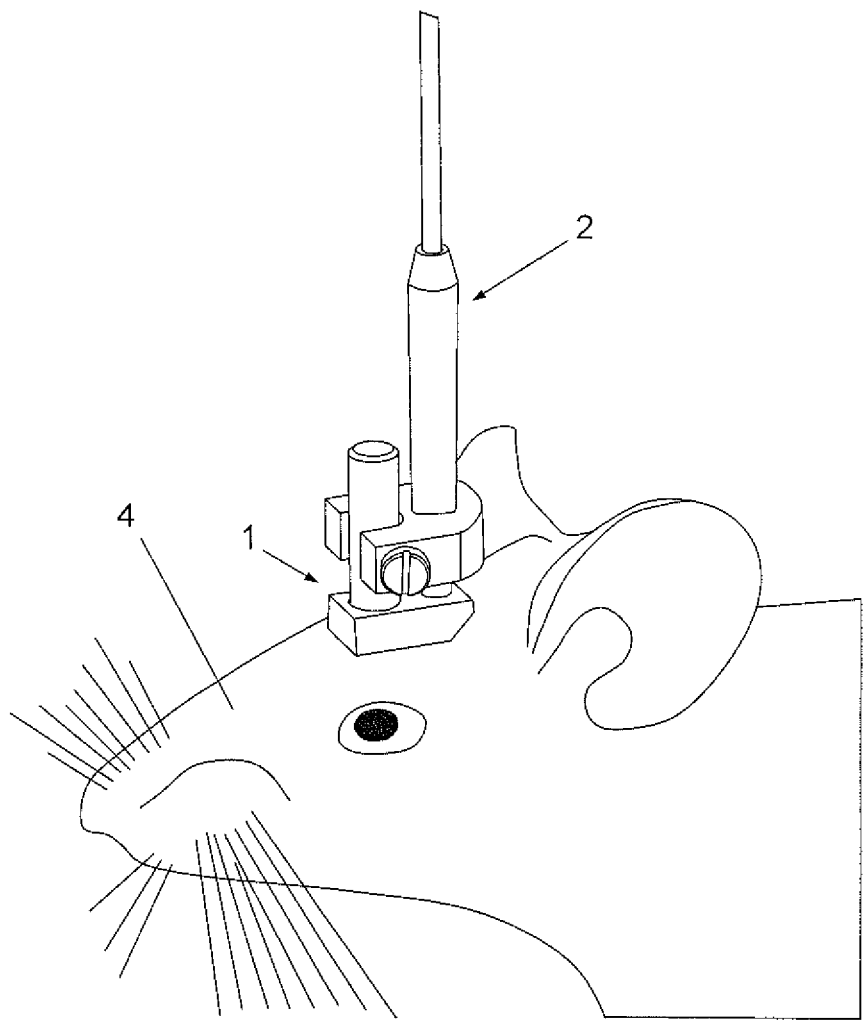
FIG. 12 is a drawing illustrating a fiber bundle probe according to an embodiment of the present disclosure inserted in an implant according to an embodiment of the present disclosure installed on a skull of a mouse.

When the implant 1 is positioned on the skull of the animal for the hollow conduit 12 to emerge onto the drilled orifice, the fiber bundle 24 may be inserted in the brain of the animal through the hollow conduit 12 of the implant 1. FIG. 12 illustrates a mouse 4 on the head of which an implant 1 receiving a fiber bundle probe 2 is installed.

Figure 11:
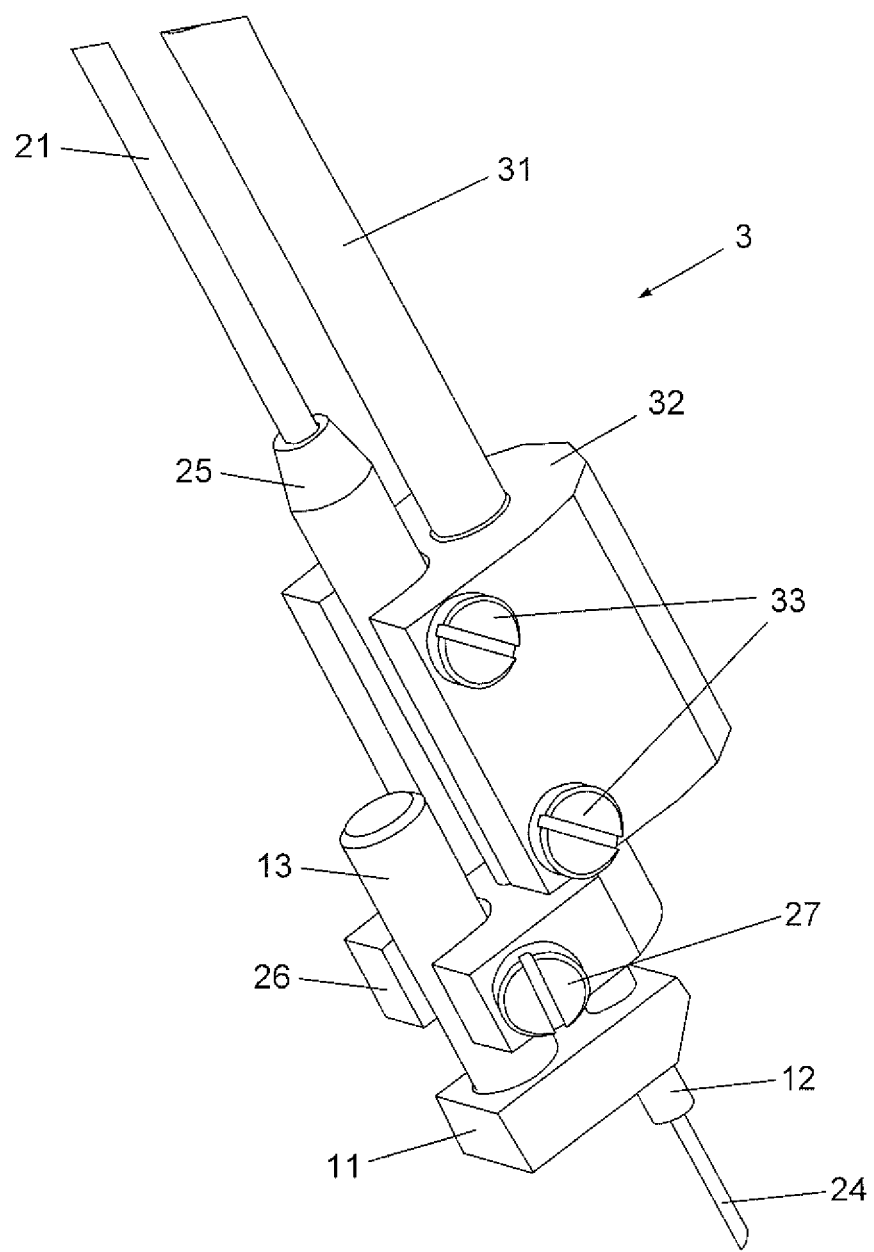
FIG. 11 is perspective view of a stereotactic device according to an embodiment of the present disclosure positioning a fiber bundle probe according to an embodiment of the present disclosure in an implant according to an embodiment of the present disclosure.

As shown on FIG. 11, the fiber bundle may be manipulated with the stereotactic device 3. The stereotactic device 3 is an interface that enables to manipulate the implant 1 and the fiber bundle within the stereotactic frame. The stereotactic device 3 may adapted to successively hold the fiber bundle and the implant in collinear directions.

Figure 3B:
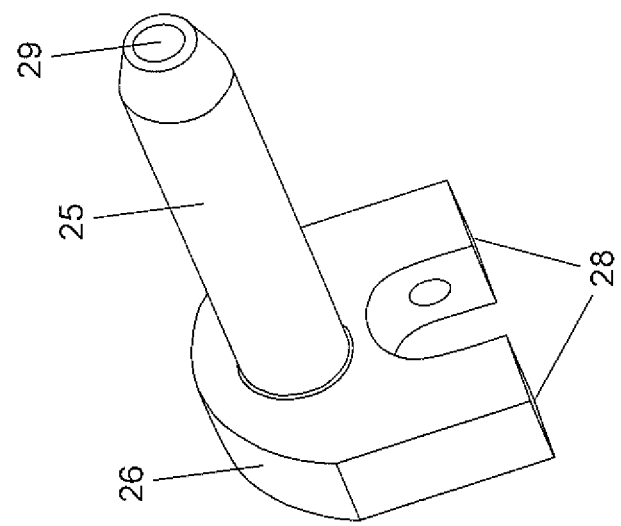
FIG. 3A and FIG. 3B illustrate front and rear perspective views of a ferrule to be arranged on a distal portion of a fiber bundle according to an embodiment of the present disclosure.
Figure 3A:
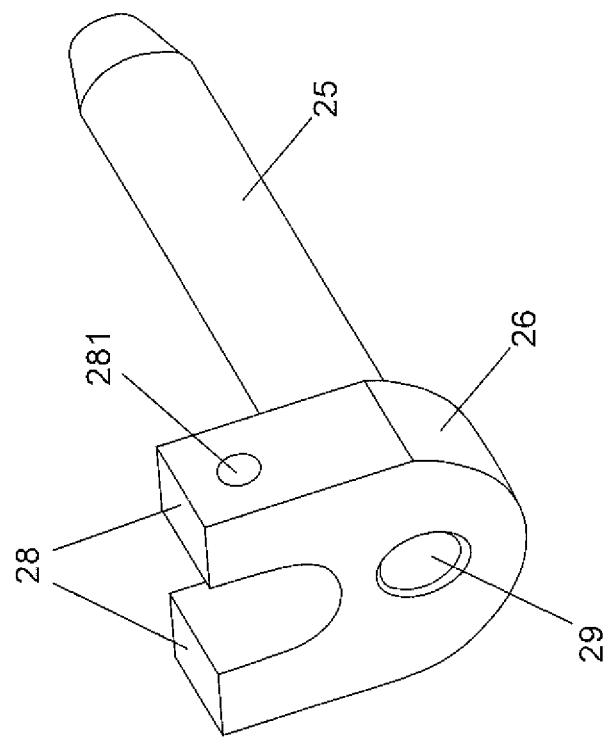
Figures 4A, 4B:
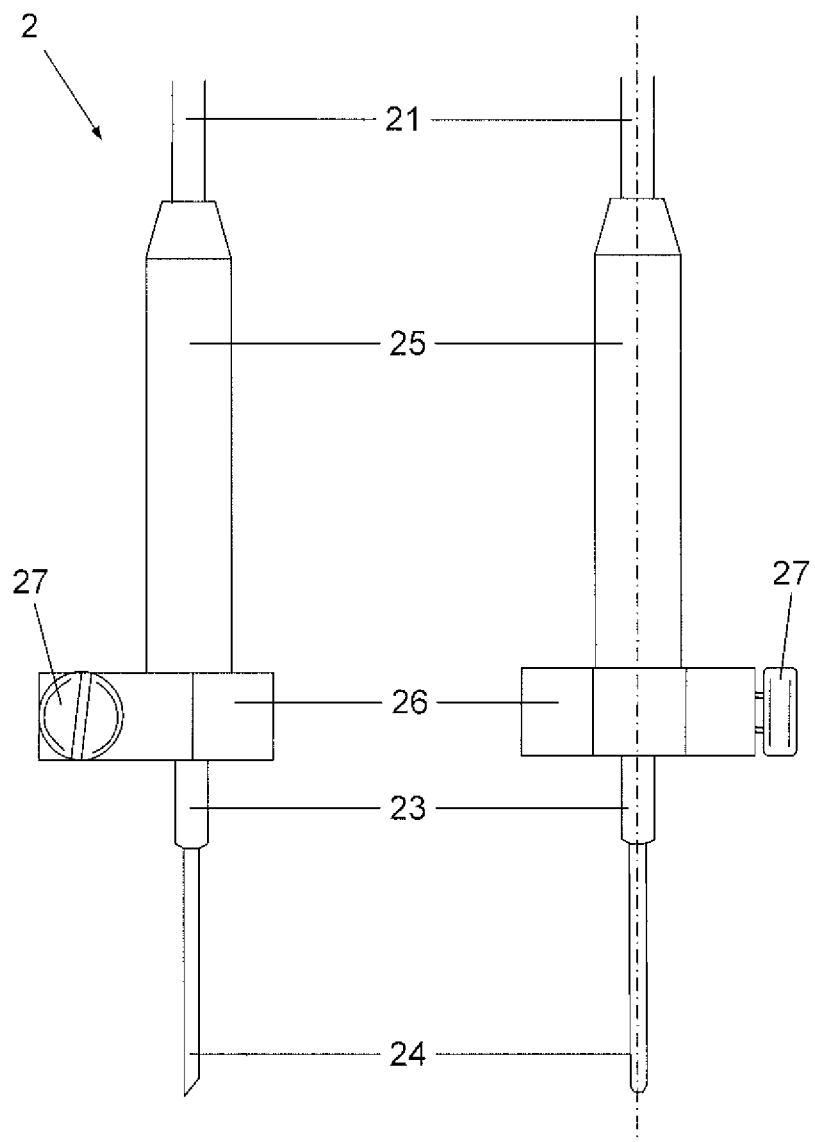
FIG. 4A and FIG. 4B illustrate lateral views of a fiber bundle probe according to an embodiment of the present disclosure.

A fiber bundle probe 2 according to an embodiment of the present disclosure is represented on FIGS. 4A and 4B. The fiber bundle probe 2 may comprise a fiber bundle 24 for transporting light and a ferrule arranged around a distal portion of the fiber bundle 24. A portion of the fiber bundle 24 may be sheathed in a sheath 21. The ferrule may comprise an handling part 25 for manipulating the fiber bundle into the hollow conduit 12 of the implant 1 and a second locking member 26 for cooperating with the first locking member 13 of the intracranial implant, to lock the fiber bundle on a determined region of the brain of the animal, when the distal tip of the fiber bundle 24 is inserted in the brain of the animal through the hollow conduit 12 of the implant 1. The distal tip of the fiber bundle to be inserted in the brain of the animal may be stripped and not covered by the ferrule. As shown on FIGS. 3A and 3B, the handling part 25 may comprise an hollow canal 29 for the fiber bundle 24 to be mounted in. The handling part 25 may extend longitudinally along the distal portion of the fiber bundle 24 and the second locking member 26 may extend laterally to the handling part 25, perpendicularly to said handling part 25.

The stereotactic device 3 may be adapted to hold the fiber bundle 24 by fastening the handling part 25 of the fiber bundle probe in the groove 32. The stereotactic device 3 may be adapted to hold the implant 1 by fastening the first locking member of the implant. The surface of the groove 32 may be adapted to successively hold the fiber bundle probe 2 and the implant 1 in collinear directions. The surface of the groove 32 may be any if a U-shaped groove or a V-shaped groove (not shown on FIGS. 10-11).

As shown on FIGS. 3A and 3B, the second locking member 26 of the ferrule may comprise two halves 28 forming an arch for the first locking member 13 to fit into, when the distal tip of the fiber bundle 24 may be inserted in the brain of the animal through the hollow conduit 12 of the implant 1. One half of the second locking member may comprise the locking screw 27 arranged in a hole 281. The locking screw 27 enables to block the first locking member 13 within the second locking member halves 28 on a determined region of the brain to image, when the distal tip of the fiber bundle 24 is inserted in the brain of the animal through the hollow conduit 12 of the implant 1. FIG. 6C is a top view of a fiber bundle probe inserted in an implant and shows how the first locking member may fit into the halves 28 of the second locking member 26 in accordance with the present embodiment.

Figure 5:
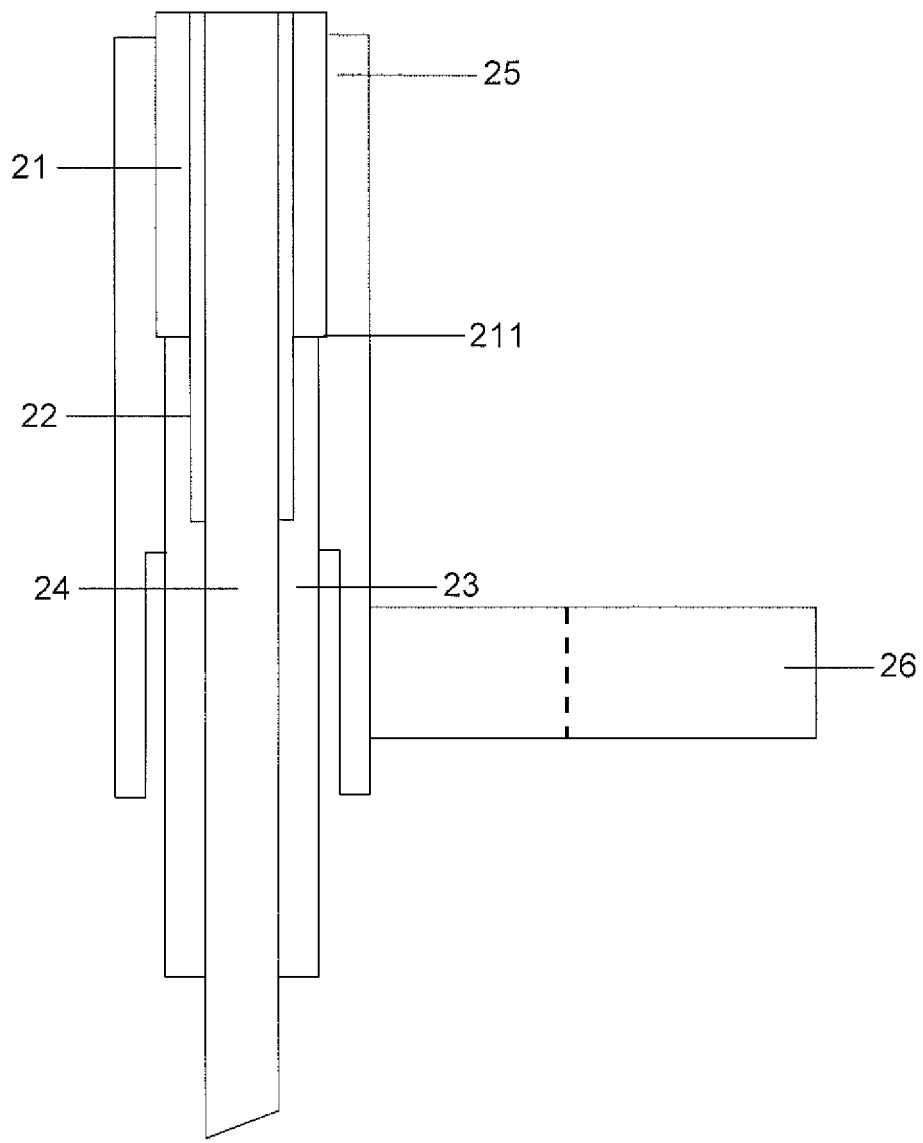
FIG. 5 illustrates schematically a transverse section of a fiber bundle probe according to an embodiment of the present disclosure.

FIG. 5 illustrates schematically a transverse section of a fiber bundle probe according to an embodiment of the present disclosure. The fiber bundle may initially comprise a coating 22 and a sheath 21 wrapping the fiber bundle 24. In order to obtain a fiber bundle probe 2, the sheath 21 may be removed on a first distal part extending from a sheath removing section 211, located in the distal portion around which the ferrule is to be arranged, to the distal tip of the fiber bundle to be inserted in the brain of the animal. The coating 22 may further be removed on a second distal part extending till the distal tip of the fiber bundle to be inserted in the brain of the animal. The second distal part may be smaller than the first distal part. A guiding sheath 23, of a specified diameter adapted to the diameter of the hollow conduit 12, may further be arranged on the fiber bundle 24. The guiding sheath 23 may extend from the sheath removing section 211 and may cover a guiding portion of the fiber bundle 24 to be inserted in the hollow conduit 12 of the implant while leaving the distal tip of the fiber bundle to be inserted in the brain of the animal uncovered. The guiding sheath 23 may be fixed to the fiber bundle 24 using glue. The ferrule may be fixed to the guiding sheath 23 using glue.

Figure 7B:
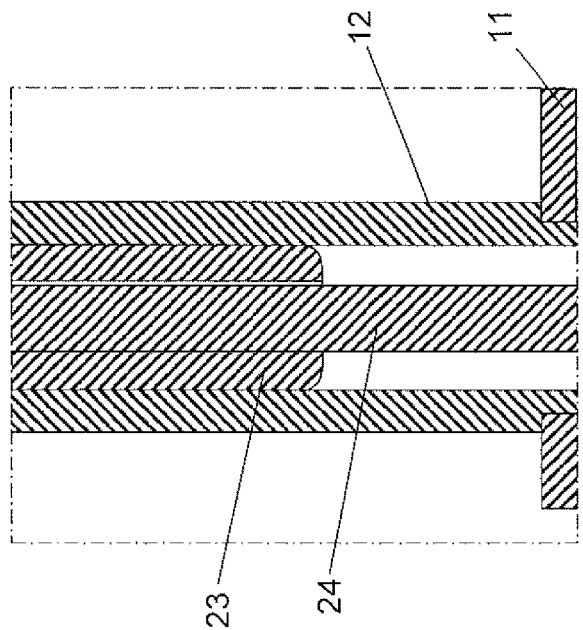
FIG. 7A and FIG. 7B are enlargement views of the marked areas highlighted in FIG. 6B.

FIG. 7B is an enlargement of the highlighted area marked C on FIG. 6B which shows a lateral section of a fiber bundle probe 2 inserted in an implant 1. FIG. 7B illustrates a lateral section of a piece of the guiding portion of the fiber bundle 24, sheathed in the guiding sheath 23, inserted in the hollow conduit 12 of the implant. As shown on FIG. 7B, the distal tip of the fiber bundle may be stripped and the guiding sheath may not extend till the distal tip of the fiber bundle to be inserted in the brain of the animal.

Figure 7A:
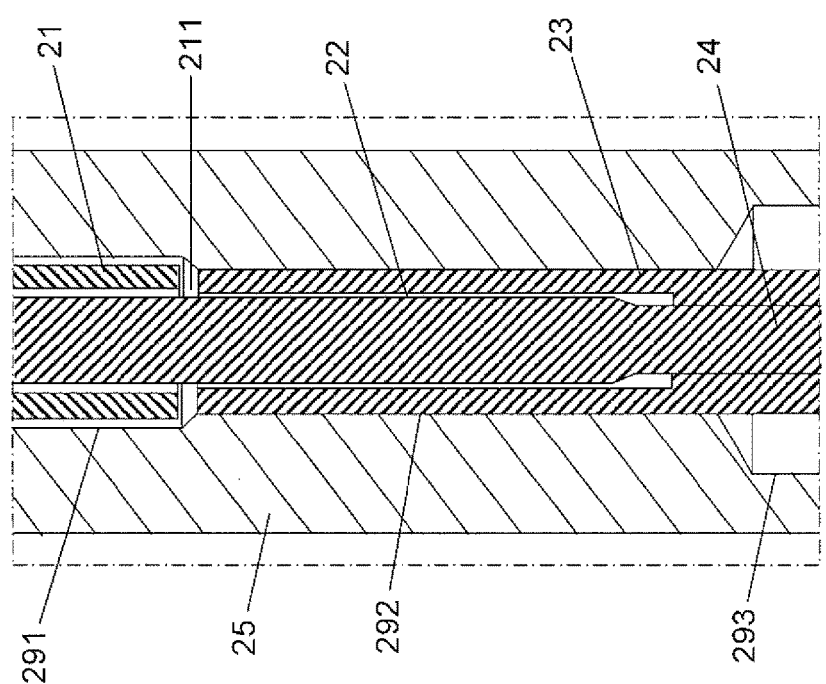

FIG. 7A is an enlargement of the highlighted area marked B on FIG. 6B. FIG. 7A illustrates a lateral section of a piece of the fiber bundle probe 2. As shown on FIG. 7A, the hollow canal 29 in which the fiber bundle is mounted may comprise an upper part 291 of an inner diameter adapted to the sheath 21, a middle part 292 of a diameter adapted to the guiding sheath 23 and a lower part 293 of a diameter superior to the diameter of the hollow conduit. This enables the fiber bundle to be inserted in the hollow conduit 12. The upper part 291 may cover a portion of the fiber bundle 24 wrapped with the sheath 21 and extends till the sheath removal section 211. The middle part 292 may cover a portion of the fiber bundle 24 covered with the guiding sheath 23. Advantageously, the ferrule is fixed to the fiber bundle by using glue at the level of the middle part 292. The lower part 293 may cover a portion of the fiber bundle covered by the guiding sheath 23 that is to be inserted in the hollow conduit 12 of the implant. This may protect the guiding portion of the fiber bundle to be inserted in the hollow conduit 12.

When the fiber bundle is positioned on the determined region of the brain to image, the first and second members may be locked for blocking the fiber bundle probe on the determined region and the animal may be woken-up and unrestrained from the stereotactic frame.

As shown on FIGS. 6A, 6B, 6C, 8 and 9, the first locking member of the implant cooperates with the second locking member of the fiber bundle probe. As previously described, the first locking member either being a pin 13 or a locking cylinder 17 mounted on a screw 16 may fit into the arch formed by the halves 28 of the second locking member 26 and may be blocked by the locking screw 27 mounted on one half of the second locking member 26. This may enable a high stability for image acquisition and may permit taking the fiber bundle out of the brain or the mouse while limiting risks of equipment damages. This enables chronic experiments to be carried out on extended period of time.

The fiber bundle probe may further comprise a rigid jacket 241 arranged at the distal tip of the fiber bundle 24. The rigid jacket 241 may be formed of a metallic material, for example stainless steel. The rigid jacket 241 may have a generally cylindrical shape and comprise a lumen adapted for the fiber bundle 24 to fit into. An external diameter of the rigid jacket 241 may be inferior to a external diameter of the guiding sheath 23. The external diameter of the rigid jacket 241 may be of around 400 to 500 μm. At a distal portion of the guiding sheath 23, an inner diameter of the guiding sheath 23 may be configured to enable the rigid jacket 241 to fit into the lumen of the guiding sheath 23. The rigid jacket may enable to strengthen the tip of fiber bundle against lateral and frontal shocks thereby easing handling and re-polishing operations by the end user.

Figure 13:
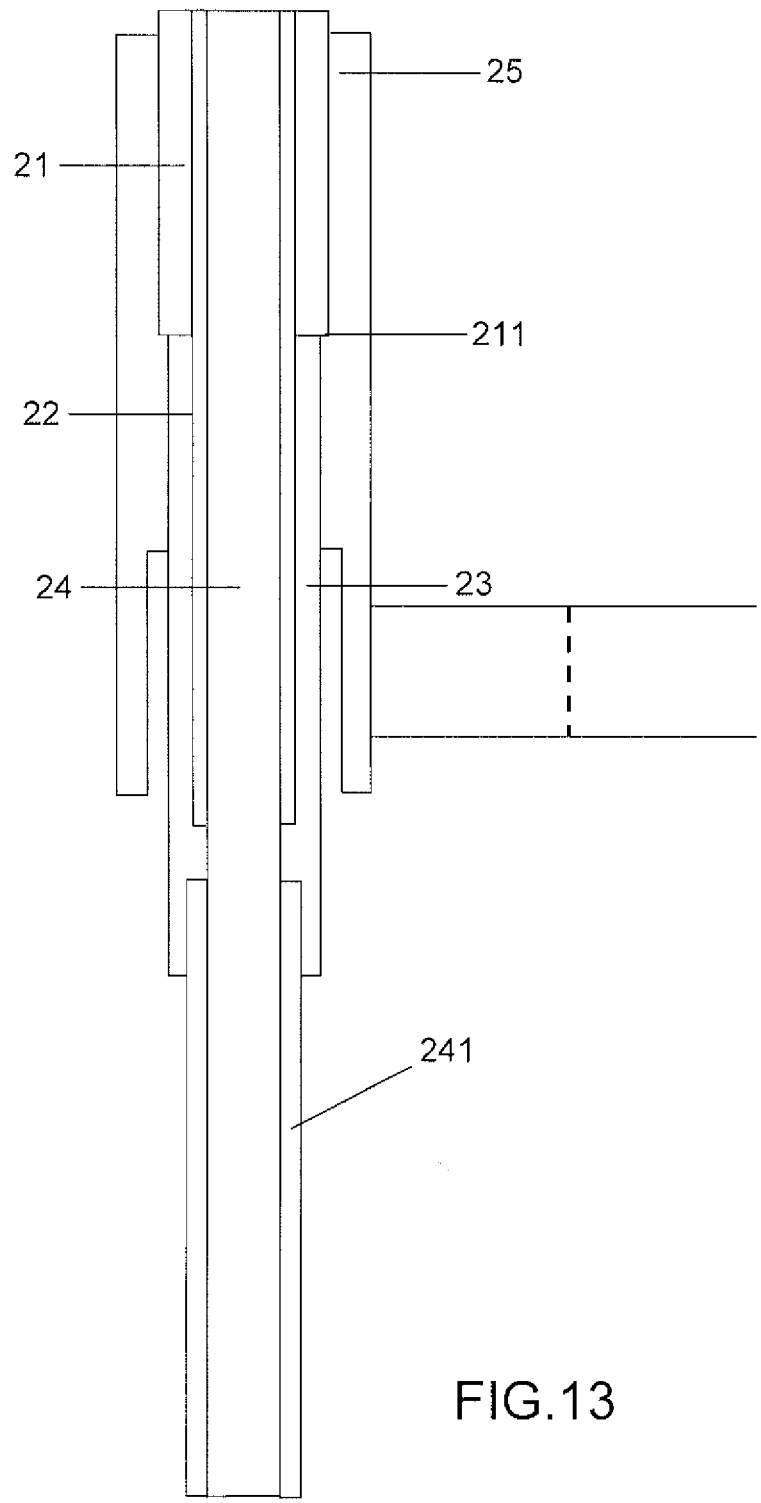
FIG. 13 illustrates schematically a transverse section of a fiber bundle probe according to an embodiment of the present disclosure.
Figure 14:
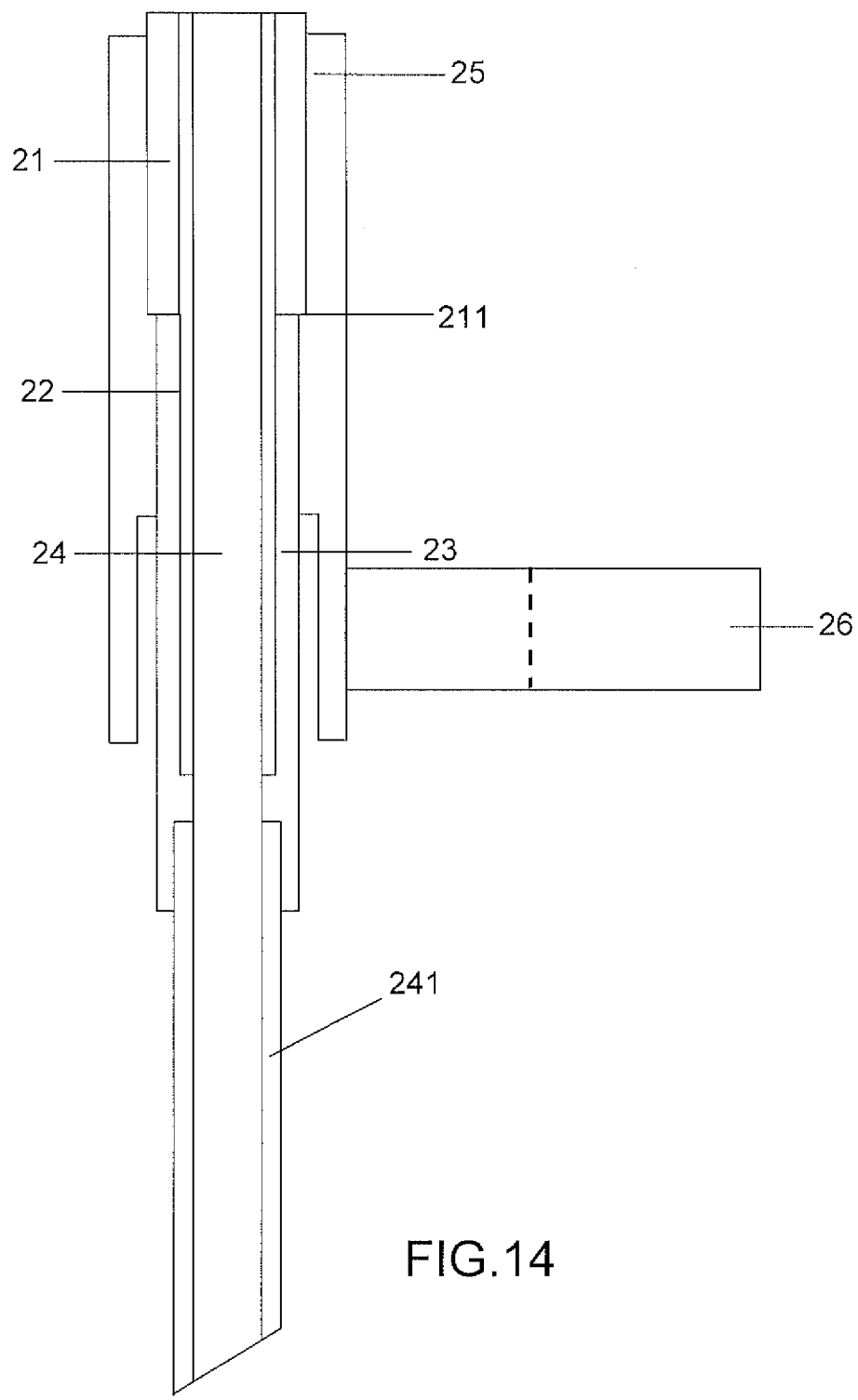
FIG. 14 illustrates schematically a transverse section of a fiber bundle probe according to an embodiment of the present disclosure.
Figure 15:
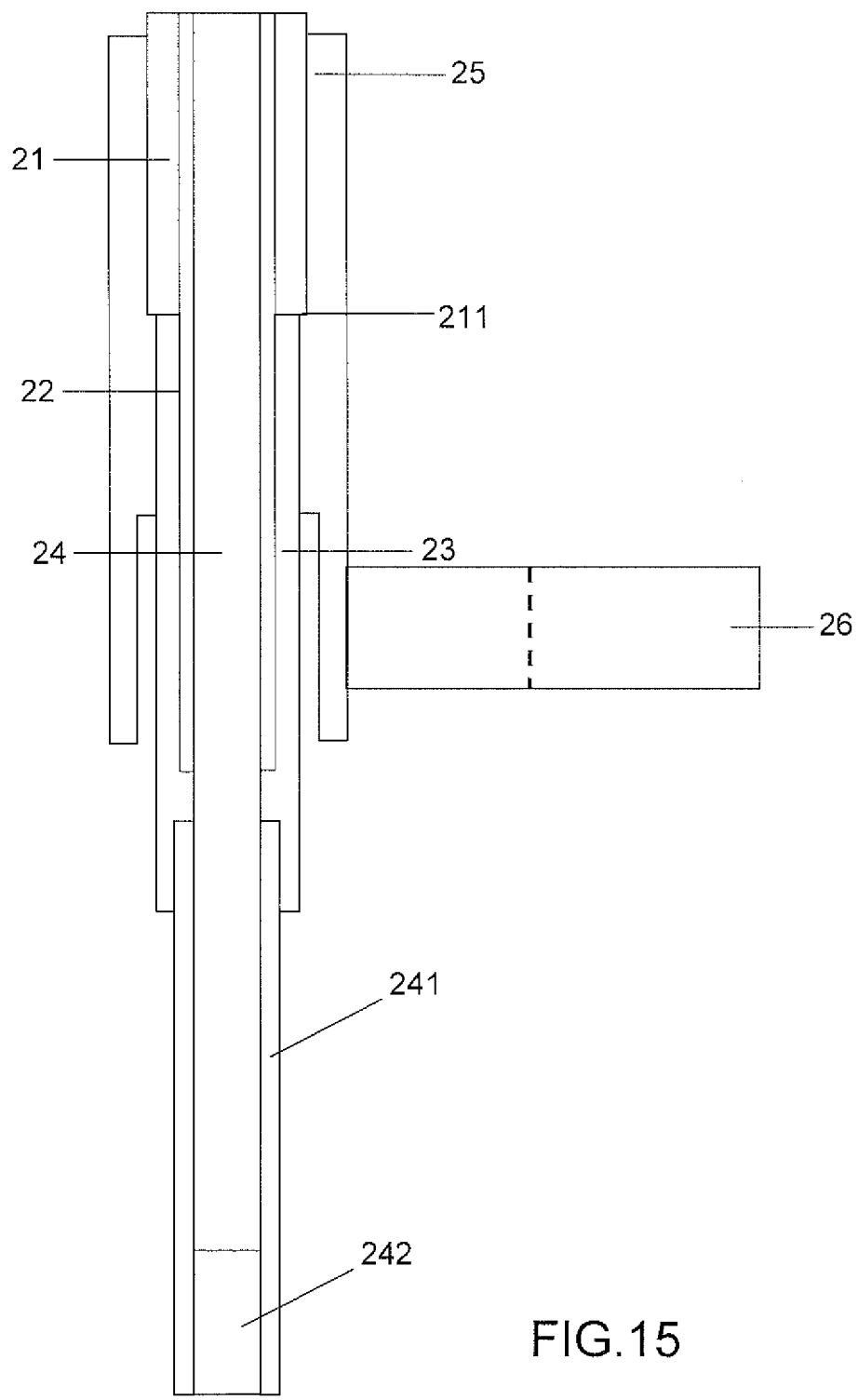
FIG. 15 illustrates schematically a transverse section of a fiber bundle probe according to an embodiment of the present disclosure.

In an embodiment illustrated on FIG. 13, the rigid jacket 241 may extend to the end of the distal tip of the fiber bundle 24. In an embodiment illustrated on FIG. 14, the rigid jacket 241 and the distal tip of the fiber bundle 24 may further be beveled. In an embodiment illustrated on FIG. 15, the rigid jacket 241 may extend beyond the end of the distal tip of the fiber bundle to cover a miniaturized objective 242 arranged at the end of the distal tip of the fiber bundle. The miniaturized objective 242 may be of a cylindrical shape and have a diameter substantially equal to the diameter of the fiber bundle. The miniaturized objective 242 may be a gradient index lens and may be connected coaxially to the fiber bundle 24, for example by using adhesive means. Alternatively, the miniaturized objective 242 may include other elements, such as conventional lenses, filters, or diffractive elements. The rigid jacket 241 may enable to strengthen the connection between the fiber bundle 24 and the miniaturized objective 242.

Figure 16A:
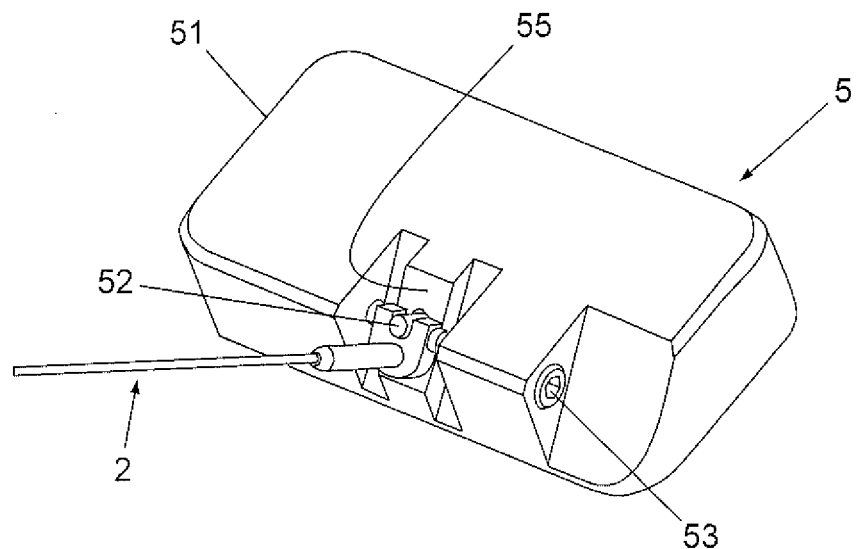
FIGS. 16A and 16B illustrate top and bottom perspective views of a polishing system according to an embodiment of the present disclosure.
Figure 16B:
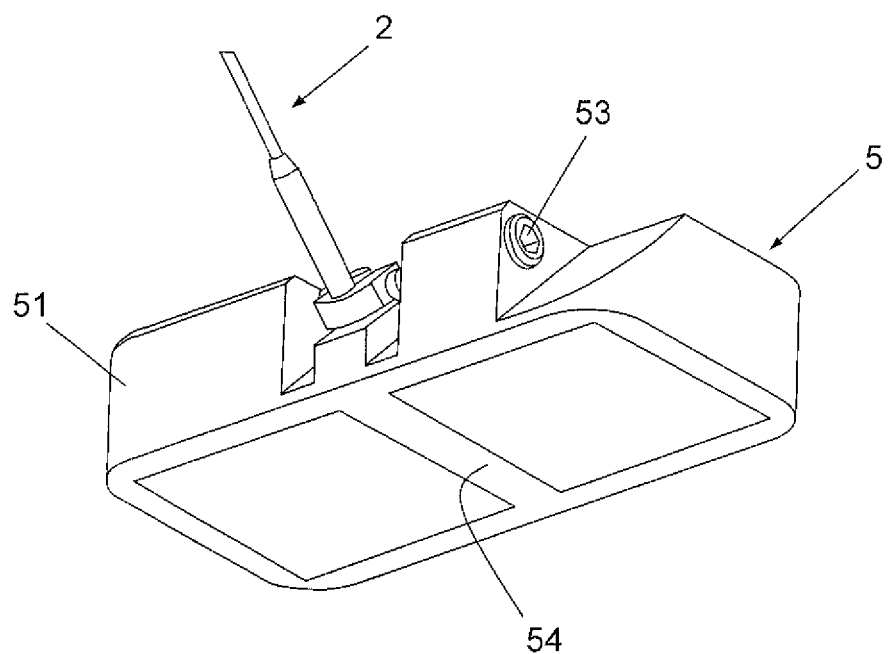

FIGS. 6A and 16B illustrate a fiber bundle probe 2 inserted into a polishing tool 5. The polishing tool 5 comprises a polishing support 51, a polishing hollow conduit (not shown on FIGS. 16A and 16B) arranged through the polishing support 51, a polishing locking member 52, arranged on the polishing support to cooperate with the ferrule of the fiber bundle probe 2 when the distal tip of the fiber bundle is inserted into the polishing hollow conduit and a supplementary locking mechanism 53 to lock the fiber bundle probe 2 on the polishing base support 51. The polishing base support 51 may be configured for the distal tip of the fiber bundle to protrude out of a polishing face 54 when the fiber bundle probe 2 is locked on the polishing support 51. The polishing of the fiber bundle may be performed by rubbing the protruding tip of the fiber bundle over a rigid surface. An insertion lace 55 of the polishing support 51 may form an angle with the polishing face 54 thereby enabling to polish the distal tip of the fiber bundle with a bevel. The polishing conduit and the polishing locking member may be arranged to reproduce the configuration of the intracranial implant. Therefore, the polishing tool 5 may hold the fiber bundle in a position identical to the position it may have when inserted in the intracranial implant. This enables, in an embodiment in which the fiber bundle is originally beveled in a determined direction, to keep said direction when re-polishing the fiber bundle with the polishing tool.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure be limited only by the attached claims.

What is claimed is:
1. A system comprising:
a fiber bundle probe having a fiber bundle; and
an intracranial implant to position the fiber bundle of the fiber bundle probe to a specified region of a brain of an animal, the implant comprising:
  a base support configured to be fixed to a skull of the animal over an orifice drilled in the skull;
  a hollow conduit arranged through the base support to guide the fiber bundle to the brain of the animal through the drilled orifice, wherein the fiber bundle is configured to transport light and comprises a distal tip to be inserted in the brain of an animal through the intracranial implant; and
  a first locking member arranged on the base support, to cooperate with a ferrule of the fiber bundle probe, said ferrule arranged on a distal portion of the fiber bundle, the first locking member configured to lock the fiber bundle to the specified region of the brain of the animal,
wherein the first locking member comprises a pin perpendicular to the base support,
wherein the pin further comprises:
  a first portion arranged in the base support comprising a first threading cooperating with a second threading of the base support, the first portion configured to adjust the position of the pin in a direction perpendicular to the base support;
  a second portion around which a locking cylinder is concentrically arranged, wherein the locking cylinder is fixed in translation with regard to a longitudinal axis of the pin and free to rotate around the axis: and
  a collar between the first portion and the second portion, wherein the first locking member further comprises a spring concentrically arranged around the pin at one end of the locking cylinder, the spring being configured to push the pin in the second threading of the base support and the locking cylinder on the collar.

2. The system according to claim 1, wherein the first locking member is arranged on the base support remote from the hollow conduit.

3. The system according to claim 1, wherein a portion of the pin is integral to the base support.

4. A system comprising:
a fiber bundle probe having a fiber bundle: and
an Intracranial implant to position the fiber bundle of the fiber bundle probe to a specified region of a brain of an animal, the implant comprising:
  a base support configured to be fixed to a skull of the animal over an orifice drilled in the skull:
  a hollow conduit arranged through the base support to guide the fiber bundle to the brain of the animal through the drilled orifice, wherein the fiber bundle is configured to transport light and comprises a distal tip to be inserted in the brain of an animal through the intracranial implant; and
  a first locking member arranged on the base support, to cooperate with a ferrule of the fiber bundle probe, said ferrule arranged on a distal portion of the fiber bundle, the first locking member configured to lock the fiber bundle to the specified region of the brain of the animal,
wherein the first locking member comprises a pin perpendicular to the base support,
wherein the pin further comprises:
  a first portion arranged in the base support, wherein the first portion is fixed in translation with respect to a longitudinal axis of the pin and wherein the first portion is free to rotate around the axis;
  a second portion comprising a first threading cooperating with a second threading of a locking cylinder concentrically arranged around said second portion, the second portion configured to adjust the position of the locking cylinder in a direction perpendicular to the base support: and
  a collar between the first portion and the second portion, wherein the first locking member further comprises a spring concentrically arranged around the pin at one end of the locking cylinder, the spring being configured to push the pin in the second threading of the locking cylinder and the locking cylinder on the collar.

\* \* \* \* \*